US012173336B2

(12) United States Patent
Madera et al.

(10) Patent No.: US 12,173,336 B2
(45) Date of Patent: Dec. 24, 2024

(54) PaCas9 NUCLEASE

(71) Applicant: JOINT STOCK COMPANY "BIOCAD", St.Petersburg (RU)

(72) Inventors: Dmitriy Aleksandrovich Madera, Moscow (RU); Aleksandr Vladimirovich Karabelskii, g.Gatchina (RU); Roman Alekseevich Ivanov, Moscow (RU); Dmitry Valentinovich Morozov, St.Petersburg (RU); Konstantin Viktorovich Severinov, Moscow (RU); Sergey Anatolevich Shmakov, G. Voskresensk (RU); Dmitrii Aleksandrovich Sutormin, Moscow (RU); Georgii Evgenevich Pobegalov, St. Petersburg (RU); Aleksandra Andreevna Vasileva, St. Petersburg (RU); Polina Anatolevna Selkova, G. Votkinsk (RU); Anatolii Nikolaevich Arseniev, St. Petersburg (RU); Tatyana Igorevna Zyubko, G. Kaliningrad (RU); Iana Vitalevna Fedorova, G. Gatchina (RU)

(*) Notice: Subject to any disclaimer, the term of this patent is extended or adjusted under 35 U.S.C. 154(b) by 698 days.

(21) Appl. No.: 17/276,016

(22) PCT Filed: Sep. 13, 2019

(86) PCT No.: PCT/RU2019/050154
§ 371 (c)(1),
(2) Date: Mar. 12, 2021

(87) PCT Pub. No.: WO2020/055293
PCT Pub. Date: Mar. 19, 2020

(65) Prior Publication Data
US 2022/0064612 A1    Mar. 3, 2022

(30) Foreign Application Priority Data

Sep. 14, 2018  (RU) ............................ 2018132816

(51) Int. Cl.
*C12N 9/22*        (2006.01)
*C12N 15/79*       (2006.01)

(52) U.S. Cl.
CPC ............... *C12N 9/22* (2013.01); *C12N 15/79* (2013.01)

(58) Field of Classification Search
None
See application file for complete search history.

(56) References Cited

U.S. PATENT DOCUMENTS 4,399,216 A    8/1983  Axel et al.
4,510,245 A    4/1985  Cousens et al.
(Continued)

FOREIGN PATENT DOCUMENTS

CA    3029132 A1    1/2018
EP    0216846 B1    1/1990
(Continued)

OTHER PUBLICATIONS

Pace et al. Sickle Cell Disease: Genetics, Cellular and Molecular Mechanisms, and Therapies. Anemia. 2012; 2012: 143594.(Year: 2012).*

(Continued)

*Primary Examiner* — Anoop K Singh
*Assistant Examiner* — Briana N Ebbinghaus
(74) *Attorney, Agent, or Firm* — Anglehart et al.

(57) ABSTRACT

The present invention relates to the field of biotechnology, molecular biology and medicine, in particular to nuclease enzyme and use thereof. More specifically, the present invention relates to PaCas9 nuclease enzyme. The invention (Continued)

also relates to a nucleic acid encoding the nuclease, a genetic construct, an expression vector, a delivery vector, which comprise the nucleic acid, a liposome comprising the nuclease or nucleic acid encoding the nuclease, a method for producing a nuclease, methods for delivery, and a host cell comprising a nucleic acid encoding the nuclease.

8 Claims, 2 Drawing Sheets

Specification includes a Sequence Listing.

(56) References Cited

U.S. PATENT DOCUMENTS

| | | | |
|---|---|---|---|
| 4,634,665 | A | 1/1987 | Axel et al. |
| 4,740,461 | A | 4/1988 | Kaufman |
| 4,912,040 | A | 3/1990 | Kaufman et al. |
| 4,959,455 | A | 9/1990 | Clark et al. |
| 4,968,615 | A | 11/1990 | Koszinowski et al. |
| 5,168,062 | A | 12/1992 | Stinski |
| 5,179,017 | A | 1/1993 | Axel et al. |
| 9,744,247 | B2 | 8/2017 | Ventosa Rull et al. |
| 2013/0326645 | A1 | 12/2013 | Cost et al. |

FOREIGN PATENT DOCUMENTS

| | | | | |
|---|---|---|---|---|
| EP | 0256055 | B1 | 8/1991 | |
| EP | 0323997 | B1 | 4/1993 | |
| EP | 0338841 | B1 | 3/1995 | |
| EP | 3350203 | A1 | 7/2018 | |
| JP | 6559063 | B2 | 8/2019 | |
| RU | 2634395 | C1 | 10/2017 | |
| RU | 2650819 | C2 | 4/2018 | |
| WO | WO-2013176772 | A1 * | 11/2013 | ........... A01H 6/4684 |
| WO | 2017/048969 | A1 | 3/2017 | |
| WO | 2018/007976 | A1 | 1/2018 | |
| WO | WO-2018172556 | A1 * | 9/2018 | ......... A61K 31/7088 |

OTHER PUBLICATIONS

Deng et al. Single nucleotide polymorphisms and cancer susceptibility. Oncotarget. 2017; 8:110635-110649 (Year: 2017).*
Nihongaki et al. Photoactivatable CRISPR-Cas9 for optogenetic genome editing. Nat Biotechnol. Jul. 2015;33(7):755-60. (Year: 2015).*
Rajagopalan et al. A Two-Step Method for Obtaining Highly Pure Cas9 Nuclease for Genome Editing, Biophysical, and Structural Studies. Methods Protoc. May 30, 2018;1(2):17 (Year: 2018).*
International application No. PCT/RU2019/050154 International Search Report dated Jan. 9, 2020 with the translation.
International application No. PCT/RU2019/050154 Written Opinion of the International Searching Authority dated Jan. 9, 2020.
Barrangou et al.,CRISPR Provides Acquired Resistance Against Viruses in Prokaryotes, Science Mar. 23, 2007:vol. 315, Issue 5819, pp. 1709-1712, DOI: 10.1126/science.1138140.
Brouns et al., Small CRISPR RNAs Guide Antiviral Defense in Prokaryotes, Science Aug. 15, 2008: vol. 321, Issue 5891, pp. 960-964, DOI: 10.1126/science.1159689.
Makarova et al., Evolution and classification of the CRISPR-Cas systems, Nature Reviews Microbiology vol. 9, pp. 467-477 (2011), Published: May 9, 2011.
Van der Oost et al., Unravelling the structural and mechanistic basis of CRISPR-Cas systems, Nature Reviews Microbiology vol. 12, pp. 479-492 (2014), Published: Jun. 9, 2014.
Jinek et al., A Programmable Dual-RNA-Guided DNA Endonuclease in Adaptive Bacterial Immunity, Science Aug. 17, 2012: vol. 337, Issue 6096, pp. 816-821, DOI: 10.1126/science.1225829.
Charpentier et al., Rewriting a genome, Nature vol. 495, pp. 50-51 (2013), Published: Mar. 6, 2013.
Jiang et al., RNA-guided editing of bacterial genomes using CRISPR-Cas systems, Nature Biotechnology vol. 31, pp. 233-239 (2013), Published: Jan. 29, 2013.
Mali et al., Cas9 as a versatile tool for engineering biology, Nature Methods vol. 10, pp. 957-963 (2013), Published: Sep. 27, 2013.
Corresponding Japanese application No. 2021-513998 Notification of reasons for refusal dated Jul. 10, 2023 (retrieved from EPO Global Dossier, translations provided).
The corresponding European application No. 19858873.3 extended European search report dated Feb. 5, 2022.
Horn Hannes et al., An Enrichment of CRISPR and Other Defense-Related Features in Marine Sponge-Associated Microbial Metagenomes. Frontiers in Microbiology, vol. 7, Nov. 8, 2016.
Nihongaki, Yuta, et al. Photoactivatable CRISPR-Cas9 for optogenetic genome editing. Nature biotechnology, vol. 33, No. 7, p. 755-760. 2015.

* cited by examiner

Fig. 1

```
                                    RuvC I
PaCas9    1  MAKTRLGIDMGTNSIGWMLYELDKNGEISEVLKAGVRIFPDGREDKTQASKNAARRVARM

PaCas9   61  NRRQRDRYLQRRTAILRYLVKFGLMPEDKTEQRKLQDIDPYSIRAKAMEEEIPPHHLGRA

PaCas9  121  IFHISQRRGYKSSRRNEENDKDGPVKSSIEEFRRQLGDKSVGQFLSELHQENKPIRARRD

PaCas9  181  GVTNNDLFHYFPDRELIEKEFNDIWQKQQQIRSQQPDKNKQILSDILTNENKQTLPEVIF
                                    Rec lobe
PaCas9  241  HQRSLKPPIIGNCQFFPTKKRIAKALPSFQRFRILQDINNLEYFDENEWHPLPSSIRDWA PaCas9  301  LHILFAGGNLTFKKLNSQMKKDGEINESAFFNLEDEKRNDIKGDFTTKTMKEIIPALWDN PaCas9  361  WDLHKQDSMILLLIGDKSIDEDKMLDEDKMLDELSSHYNLSEEEAQECANANIDNRQGVS PaCas9  421  GRASLSLEAISILIPYLEKGNHYDKALAESGIEKDKSSKHDDHFYMQPYPEILGQWCLPR
                                    RuvC II
PaCas9  481  KSEDESNKELWRIPNPTVHVALNQLRAVVNDCIRINGGEKPSQVVVELARDLPIGIATRQ PaCas9  541  EIRKKQSENQRARTQRRNKIEELGERASAKSMLRMQLWEESSPKNANNHCCLYCGKQIGC
                                    HNH
PaCas9  601  AAAVSSPDFEIDHILPFSKTLDDSAANKTLCCVQCNREKGNKTPYEAWGSNEKRYDEIKT PaCas9  661  RASALSPKKRRRFLPDAMKHFDGDNDFLARQLTDTQYIAKVTKRYFESIIKPNDVYVIPG
                                    RuvC III
PaCas9  721  RLTEILRRKWGLNNILNDDGHKNRDDHRHHAVDAAVIGATTRSTLQKFATEAGKDNSDLP PaCas9  781  NVSITAPMKVFREKVEKTVKNIVVSHKPDRFESGALHNDTAYGLPADYKEGAGAQFVRHR PaCas9  841  IMLSDITTNFSQKVVNSFLREELKTLCDYATDKKSLDQELKRYGEKNNIRRVLIEEKLSV PaCas9  901  IAVCDKDGKPYKGYKSDSNWAYEIFEKFPNGNWDGEIISTFNANQEKFTPLWKEKNPKAK PaCas9  961  LIMRLHKNDMVALDDNGLRKICYVKTLSASKIAMVEHFDATPGRNPPTIITKSPNEPRKI PaCas9 1021  NGRKIHISPGGLVRDTKKDGRSNH
```

Fig. 2

SEQUENCE LISTING

```
<160> NUMBER OF SEQ ID NOS: 4

<210> SEQ ID NO 1
<211> LENGTH: 3135
<212> TYPE: DNA
<213> ORGANISM: Homoeodictya palmata

<400> SEQUENCE: 1
atggcaaaaa cacggcttgg tattgatatg gggactaatt ctatcggttg gatgttgtat      60
gaattggaca aaaacggtga aatttcggaa gttttaaagg cagggtgcg cattttccct     120
```

```
gatgggcgcg aggataaaac ccaagcatcc aaaaacgcgg cacggcgggt agcacgaatg      180
aatcgccgtc agcgagaccg ctatcttcag cgccggacag cgattttacg ctatttggta      240
aaatttgggc tgatgccaga agataaaaca gaacaacgaa aattgcagga tattgacccc      300
tatagtattc gtgccaaggc aatggaagaa gaaattccac cccatcatct tgggcgggca      360
atttttcata tcagccaaag acgtggctat aagagtagcc gtcgtaatga agaaaacgat      420
aaagatggtc cagtaaaaag ttccattgaa gaattccggc ggcagctggg cgacaaaagt      480
gtgggacaat ttttatctga attacaccaa gaaaataaac caatccgcgc ccgccgtgat      540
ggcgtaacta ataatgatct ttttcattat ttcccagacc cgcgaactaat tgaaaaagag      600 tttaacgata tttggcaaaa acaacaacaa atccgctcgc aacaaccaga taaaaataaa      660
caaattttat ctgatatatt aacaaatgaa aataaacaaa cttttatttga agttattttt      720 catcagcgct cttttaaagcc gccaattatc ggcaattgtc aattttttcc gaccaaaaaa      780
agaatcgcta aggcgttgcc ttcctttcag cgattccgta ttttgcagga tattaataac      840
cttgaatatt ttgatgaaaa cgagtggcac cctttgccgt cgtctattcg tgattgggca      900
ttgcacattc tttttgcggg aggtaatcta acttttaaga agttaaatag ccaaatgaag      960
aaagatggtg aaattaacga atctgcattt tttaacttag aagatgaaaa acgcaatgat     1020
attaaaggcg actttaccac caaaaccatg aaagaaatta tccccgcatt gtgggataac     1080
tgggatttgc acaaacaaga cagcatgatt ttattactaa taggagataa agtatagat     1140 gaagataaaa tgttagatga agataaaatg ttagatgaac tttcgtctca ttataattta     1200
tctgaagaag aggcacaaga atgtgcgaat gccaatattg acaacaggca aggcgttagt     1260
ggaagagcga gttatcgct agaagcgata agcatactaa taccctatttt ggaaaaagga     1320 aaccactatg ataaagcact tgctgagtcg ggaattgaaa aagataagtc ctctaaacat     1380
gatgaccatt tctatatgca gcccacccc gaaatattag gcaatggtg tttgccgcgc     1440 aaaagcgagg atgaaagcaa caagaattg tggcgtatcc cgaatccaac agtgcatgtt     1500
gcattaaatc aattgcgggc agttgttaac gactgcataa gaatcaatgg cggagaaaaa     1560
ccttcacaag ttgttgtgga gttggcacgt gacttgccaa taggtattgc aacacggcaa     1620
gaaattagaa aaaacagtc agaaaatcaa agggcacgaa cacaacgccg caataaaatt     1680
gaagaactcg gagagcgtgc gagtgctaaa tctatgttgc gcatgcaatt gtgggaagaa     1740
tcgtctccca aaaatgccaa taatcactgt tgcctatatt gtggaaaaca aataggctgc     1800
gctgccgctg tctcttctcc cgattttgag attgaccata ttctaccttt ttctaaaact     1860
ttggatgata gcgccgccaa caaaacgctt tgctgcgtcc aatgcaaccg cgaaaaagga     1920
aataaaactc cttatgaagc atggggcagt aatgaaaaac ggtatgatga aattaaaacg     1980
agagcaagtg ccctatcgcc aaaaaaacga cggcgttttt tgccagacgc aatgaaacat     2040
tttgacggtg ataacgattt tctcgctcgc caactaaccg atacgcaata tatcgccaaa     2100
gtgacgaagc gttattttga atctattata aaacccaatg atgtttatgt tattcctggt     2160
cgtttaactg aaatattaag acgcaagtgg ggattgaata atattttgaa tgatgacgga     2220
cacaaaaacc gtgatgacca tagacatcat gccgttgatg cagcagtcat tggtgcgacc     2280
actcgttcta cgctccaaaa atttgctact gaggcaggca aagacaactc cgatttacca     2340
aatgtctcta tcaccgcacc aatgaaagta tttcgtgaaa aggtggaaaa gaccgtaaaa     2400
aatattgttg tctcacacaa accagatcgt tttgagagtg gcgcgttaca taatgatact     2460
```

-continued

```
gcttatgggt tgcctgctga ttataaagaa ggtgctggtg cacaattcgt aagacatcgg    2520
attatgttgt ctgatataac tacaaatttt tctcaaaaag tggttaattc tttcttgcgc    2580
gaagaattga aaacattatg cgactatgca acggataaaa aatctttaga tcaagaatta    2640
aaacgctatg gagaaaaaaa taatattcgc cgtgttttaa tagaagaaaa attgtctgtt    2700
attgctgttt gcgataagga cggcaaaccc tataaaggtt ataaaagcga cagtaattgg    2760
gcctatgaga ttttgagaa atttcccaat ggaaattggg atggcgaaat tatttccaca    2820
tttaatgcta atcaagaaaa atttacgccc ttatggaaag aaaaaaatcc caaggctaaa    2880
cttatcatgc gcttgcacaa aaatgacatg gtagcattag atgacaatgg actacgaaaa    2940
atatgttatg taaaaacatt aagtgctagc aaaattgcca tggttgaaca ttttgatgcc    3000
actcctggta gaaatccacc tactattata accaaaagtc caaacgaatt tcgcaaaatc    3060
aatggacgaa aaatccatat tagccctggc gggttagtaa gagacactaa aaaagatggc    3120
cgatcaaatc attga                                                     3135
```

<210> SEQ ID NO 2
<211> LENGTH: 1044
<212> TYPE: PRT
<213> ORGANISM: Homoeodictya palmata

<400> SEQUENCE: 2

```
Met Ala Lys Thr Arg Leu Gly Ile Asp Met Gly Thr Asn Ser Ile Gly
 1               5                  10                  15

Trp Met Leu Tyr Glu Leu Asp Lys Asn Gly Glu Ile Ser Glu Val Leu
                20                  25                  30

Lys Ala Gly Val Arg Ile Phe Pro Asp Gly Arg Glu Asp Lys Thr Gln
            35                  40                  45

Ala Ser Lys Asn Ala Ala Arg Arg Val Ala Arg Met Asn Arg Arg Gln
        50                  55                  60

Arg Asp Arg Tyr Leu Gln Arg Arg Thr Ala Ile Leu Arg Tyr Leu Val
    65                  70                  75                  80

Lys Phe Gly Leu Met Pro Glu Asp Lys Thr Glu Gln Arg Lys Leu Gln
                85                  90                  95

Asp Ile Asp Pro Tyr Ser Ile Arg Ala Lys Ala Met Glu Glu Ile
                100                 105                 110

Pro Pro His His Leu Gly Arg Ala Ile Phe His Ile Ser Gln Arg Arg
            115                 120                 125

Gly Tyr Lys Ser Ser Arg Arg Asn Glu Glu Asn Asp Lys Asp Gly Pro
        130                 135                 140

Val Lys Ser Ser Ile Glu Glu Phe Arg Arg Gln Leu Gly Asp Lys Ser
145                 150                 155                 160

Val Gly Gln Phe Leu Ser Glu Leu His Gln Glu Asn Lys Pro Ile Arg
                165                 170                 175

Ala Arg Arg Asp Gly Val Thr Asn Asn Asp Leu Phe His Tyr Phe Pro
            180                 185                 190

Asp Arg Glu Leu Ile Glu Lys Glu Phe Asn Asp Ile Trp Gln Lys Gln
        195                 200                 205

Gln Gln Ile Arg Ser Gln Pro Asp Lys Asn Lys Gln Ile Leu Ser
    210                 215                 220

Asp Ile Leu Thr Asn Glu Asn Lys Gln Thr Leu Phe Glu Val Ile Phe
225                 230                 235                 240

His Gln Arg Ser Leu Lys Pro Pro Ile Ile Gly Asn Cys Gln Phe Phe
                245                 250                 255
```

```
Pro Thr Lys Lys Arg Ile Ala Lys Ala Leu Pro Ser Phe Gln Arg Phe
        260                 265                 270

Arg Ile Leu Gln Asp Ile Asn Leu Glu Tyr Phe Asp Glu Asn Glu
        275                 280                 285

Trp His Pro Leu Pro Ser Ser Ile Arg Asp Trp Ala Leu His Ile Leu
        290                 295                 300

Phe Ala Gly Gly Asn Leu Thr Phe Lys Lys Leu Asn Ser Gln Met Lys
305                 310                 315                 320

Lys Asp Gly Glu Ile Asn Glu Ser Ala Phe Phe Asn Leu Glu Asp Glu
                325                 330                 335

Lys Arg Asn Asp Ile Lys Gly Asp Phe Thr Thr Lys Thr Met Lys Glu
        340                 345                 350

Ile Ile Pro Ala Leu Trp Asp Asn Trp Asp Leu His Lys Gln Asp Ser
        355                 360                 365

Met Ile Leu Leu Leu Ile Gly Asp Lys Ser Ile Asp Glu Asp Lys Met
        370                 375                 380

Leu Asp Glu Asp Lys Met Leu Asp Glu Leu Ser Ser His Tyr Asn Leu
385                 390                 395                 400

Ser Glu Glu Glu Ala Gln Glu Cys Ala Asn Ala Asn Ile Asp Asn Arg
                405                 410                 415

Gln Gly Val Ser Gly Arg Ala Ser Leu Ser Leu Glu Ala Ile Ser Ile
        420                 425                 430

Leu Ile Pro Tyr Leu Glu Lys Gly Asn His Tyr Asp Lys Ala Leu Ala
        435                 440                 445

Glu Ser Gly Ile Glu Lys Asp Lys Ser Ser Lys His Asp Asp His Phe
        450                 455                 460

Tyr Met Gln Pro Tyr Pro Glu Ile Leu Gly Gln Trp Cys Leu Pro Arg
465                 470                 475                 480

Lys Ser Glu Asp Glu Ser Asn Lys Glu Leu Trp Arg Ile Pro Asn Pro
                485                 490                 495

Thr Val His Val Ala Leu Asn Gln Leu Arg Ala Val Val Asn Asp Cys
        500                 505                 510

Ile Arg Ile Asn Gly Gly Glu Lys Pro Ser Gln Val Val Val Glu Leu
        515                 520                 525

Ala Arg Asp Leu Pro Ile Gly Ile Ala Thr Arg Gln Glu Ile Arg Lys
        530                 535                 540

Lys Gln Ser Glu Asn Gln Arg Ala Arg Thr Gln Arg Arg Asn Lys Ile
545                 550                 555                 560

Glu Glu Leu Gly Glu Arg Ala Ser Ala Lys Ser Met Leu Arg Met Gln
                565                 570                 575

Leu Trp Glu Glu Ser Ser Pro Lys Asn Ala Asn Asn His Cys Cys Leu
        580                 585                 590

Tyr Cys Gly Lys Gln Ile Gly Cys Ala Ala Ala Val Ser Ser Pro Asp
        595                 600                 605

Phe Glu Ile Asp His Ile Leu Pro Phe Ser Lys Thr Leu Asp Asp Ser
        610                 615                 620

Ala Ala Asn Lys Thr Leu Cys Cys Val Gln Cys Asn Arg Glu Lys Gly
625                 630                 635                 640

Asn Lys Thr Pro Tyr Glu Ala Trp Gly Ser Asn Glu Lys Arg Tyr Asp
                645                 650                 655

Glu Ile Lys Thr Arg Ala Ser Ala Leu Ser Pro Lys Lys Arg Arg Arg
        660                 665                 670
```

-continued

```
Phe Leu Pro Asp Ala Met Lys His Phe Asp Gly Asp Asn Asp Phe Leu
            675                 680                 685
Ala Arg Gln Leu Thr Asp Thr Gln Tyr Ile Ala Lys Val Thr Lys Arg
        690                 695                 700
Tyr Phe Glu Ser Ile Ile Lys Pro Asn Asp Val Tyr Val Ile Pro Gly
705                 710                 715                 720
Arg Leu Thr Glu Ile Leu Arg Arg Lys Trp Gly Leu Asn Asn Ile Leu
                725                 730                 735
Asn Asp Asp Gly His Lys Asn Arg Asp His Arg His His Ala Val
            740                 745                 750
Asp Ala Ala Val Ile Gly Ala Thr Thr Arg Ser Thr Leu Gln Lys Phe
        755                 760                 765
Ala Thr Glu Ala Gly Lys Asp Asn Ser Asp Leu Pro Asn Val Ser Ile
    770                 775                 780
Thr Ala Pro Met Lys Val Phe Arg Glu Lys Val Glu Lys Thr Val Lys
785                 790                 795                 800
Asn Ile Val Val Ser His Lys Pro Asp Arg Phe Glu Ser Gly Ala Leu
                805                 810                 815
His Asn Asp Thr Ala Tyr Gly Leu Pro Ala Asp Tyr Lys Glu Gly Ala
            820                 825                 830
Gly Ala Gln Phe Val Arg His Arg Ile Met Leu Ser Asp Ile Thr Thr
        835                 840                 845
Asn Phe Ser Gln Lys Val Val Asn Ser Phe Leu Arg Glu Glu Leu Lys
    850                 855                 860
Thr Leu Cys Asp Tyr Ala Thr Asp Lys Lys Ser Leu Asp Gln Glu Leu
865                 870                 875                 880
Lys Arg Tyr Gly Glu Lys Asn Asn Ile Arg Arg Val Leu Ile Glu Glu
                885                 890                 895
Lys Leu Ser Val Ile Ala Val Cys Asp Lys Asp Gly Lys Pro Tyr Lys
            900                 905                 910
Gly Tyr Lys Ser Asp Ser Asn Trp Ala Tyr Glu Ile Phe Glu Lys Phe
        915                 920                 925
Pro Asn Gly Asn Trp Asp Gly Glu Ile Ile Ser Thr Phe Asn Ala Asn
    930                 935                 940
Gln Glu Lys Phe Thr Pro Leu Trp Lys Glu Lys Asn Pro Lys Ala Lys
945                 950                 955                 960
Leu Ile Met Arg Leu His Lys Asn Asp Met Val Ala Leu Asp Asp Asn
                965                 970                 975
Gly Leu Arg Lys Ile Cys Tyr Val Lys Thr Leu Ser Ala Ser Lys Ile
            980                 985                 990
Ala Met Val Glu His Phe Asp Ala Thr Pro Gly Arg Asn Pro Pro Thr
        995                 1000                1005
Ile Ile Thr Lys Ser Pro Asn Glu Phe Arg Lys Ile Asn Gly Arg Lys
    1010                1015                1020
Ile His Ile Ser Pro Gly Gly Leu Val Arg Asp Thr Lys Lys Asp Gly
1025                1030                1035                1040
Arg Ser Asn His

<210> SEQ ID NO 3
<211> LENGTH: 120
<212> TYPE: RNA
<213> ORGANISM: Homoeodictya palmata

<400> SEQUENCE: 3
```

```
tataacaaac aaagaaatgc ggtttattta acattaacat gtgataaatt cgcaacaacc         60
tttagggcaa cttcggttgc cctattgctt ttaatggcga tataaatatt ttattaatcc        120

<210> SEQ ID NO 4
<211> LENGTH: 36
<212> TYPE: DNA
<213> ORGANISM: Homoeodictya palmata

<400> SEQUENCE: 4
gttgtgttat gaccgcattt ctttgtttgg tataat                                   36
```

PaCas9 NUCLEASE

FIELD OF THE INVENTION

The present invention relates to the field of biotechnology, molecular biology and medicine, in particular to nuclease enzyme and use thereof. More specifically, the present invention relates to PaCas9 nuclease enzyme. The invention also relates to a nucleic acid encoding said nuclease, a genetic construct, an expression vector, a delivery vector, which comprise said nucleic acid, a liposome comprising said nuclease or nucleic acid encoding said nuclease, a method for producing a nuclease, methods for delivery, and a host cell comprising a nucleic acid encoding said nuclease.

BACKGROUND

In 2007, it was first shown that CRISPR-Cas is an adaptive immune system in many bacteria and most of archaea (Barrangou et al., 2007, Science 315:17091712, Brouns et al., 2008, Science 321:960-964). Based on functional and structural criteria, three types of CRISPR-Cas systems have so far been characterized, most of which use small RNA molecules as guide to target complementary DNA sequences (Makarova et al., 2011, Nat Rev Microbiol 9:467-477, Van der Oost et al., 2014, Nat Rev Microbiol 12:479-492).

In a recent study by the Doudna/Charpentier labs, a thorough characterization of the effector enzyme of the type II CRISPR-Cas system (Cas9) was performed, including demonstration that the introduction of designed CRISPR RNA guides (with specific spacer sequences) targets complementary sequences (protospacers) on a plasmid, causing double strand breaks of this plasmid (Jinek et al., 2012, Science 337:816-821). Later, Jinek et al., 2012 used Cas9 as a tool for genome editing.

Cas9 has been used to engineer the genomes of a range of eukaryotic cells (e.g. fish, plant, man) (Charpentier and Doudna, 2013, Nature 495:50-51).

Moreover, Cas9 has been used to improve yields of homologous recombination in bacteria by selecting for dedicated recombination events (Jiang et al., 2013, Nature Biotechnol 31:233-239). To achieve this, a toxic fragment (targeting construct) is co-transfected with a rescuing fragment carrying the desired alteration (editing construct, carrying point mutation or deletions). The targeting construct consists of Cas in combination with a design CRISPR and an antibiotic resistance marker, defining the site of the desired recombination on the host chromosome; in the presence of the corresponding antibiotic, integration of the targeting construct in the host chromosome is selected. Only when the additional recombination occurs of the editing construct with the CRISPR target site elsewhere on the host chromosome, the host can escape from the auto-immunity problem. Hence, in the presence of the antibiotic, only the desired (marker-free) mutants are able to survive and grow. A related strategy to select for subsequent removal of the integrated targeting construct from the chromosome is presented as well, generating a genuine marker-free mutant.

It has been established in recent years that CRISPR-Cas-mediated genome editing constitutes a useful tool for genetic engineering. It has been established that the prokaryotic CRISPR systems serve their hosts as adaptive immune systems (Jinek et al., 2012, Science 337:816-821) and can be used for quick and effective genetic engineering (for example, Mali et al., 2013, Nat Methods 10:957-963), requiring only modification of the guide sequence in order to target sequences of interest.

However, there is a continuing need for the development of agents with improved sequence-specific nucleic acid detection, cleavage and manipulation under a variety of experimental conditions for application in the area of genetic research and genome editing.

BRIEF SUMMARY OF INVENTION

The present invention relates to PaCas9 nuclease having an amino acid sequence of SEQ ID NO: 2.

In one aspect, the present invention relates to an isolated nucleic acid molecule encoding PaCas9 nuclease having the nucleotide sequence of SEQ ID NO: 1.

In one aspect, the present invention relates to an expression vector comprising nucleic acid having the nucleotide sequence of SEQ ID NO: 1.

Figure 1:
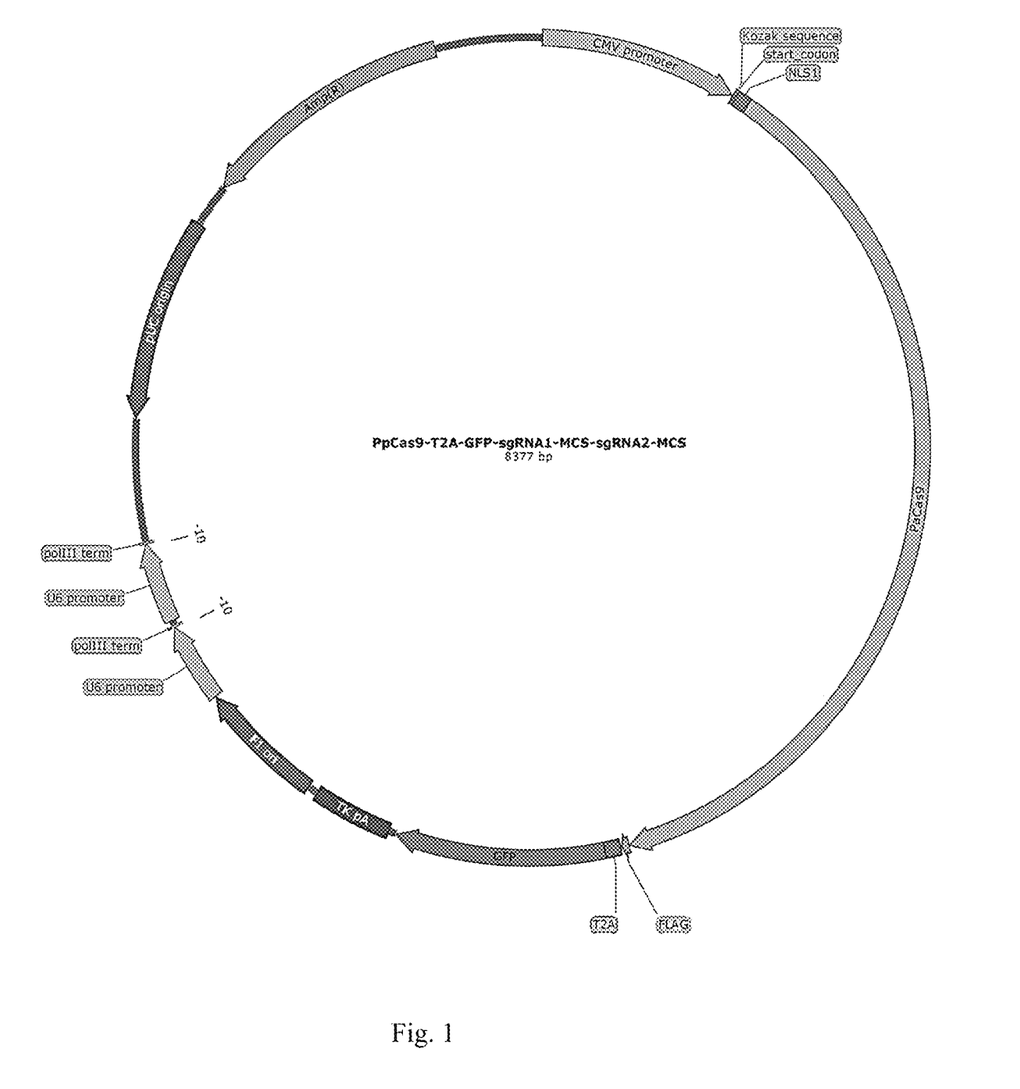
FIG. 1 Circular scheme of plasmid PpCas9-T2A-GFP-sgRNA1-MCS-sgRNA2-MCS intended for production of PpCas9 nuclease in mammalian cells.

In some embodiments, the expression vector is a genetic construct as shown in FIG. 1, PpCas9-T2A-GFP-sgRNA1-MCS-sgRNA2-MCS.

In one aspect, the present invention relates to a vector to deliver a therapeutic agent comprising nucleic acid having the nucleotide sequence of SEQ ID NO: 1.

In one embodiment of the present invention, the vector delivers the therapeutic agent to target cells or target tissues.

In one aspect, the present invention relates to a liposome to deliver a therapeutic agent comprising PaCas9 nuclease having an amino acid sequence of SEQ ID NO: 2 nucleic acid having the nucleotide sequence of SEQ ID NO: 1.

In one embodiment of the present invention, the liposome delivers the therapeutic agent to target cells or target tissues.

In one aspect, the present invention relates to a method for delivering a therapeutic agent to target cells or target tissues using the above vector or the above liposome.

In one embodiment of the method, the therapeutic agent is delivered to the target cells or target tissues by way of administering the above vector or the above liposome into a mammalian body.

In one aspect, the present invention relates to a method for producing a host cell to produce PaCas9 nuclease having an amino acid sequence of SEQ ID NO: 2, which includes transformation of the cell using any of the above vector.

In one aspect, the present invention relates to a method for producing the PaCas9 nuclease, which comprises culturing the above host cell in a growth medium under conditions sufficient to produce said PaCas9 nuclease, if necessary, followed by isolation and purification of the obtained PaCas9 nuclease.

BRIEF DESCRIPTION OF DRAWINGS

AmpR is a beta-lactamase gene that provides resistance to ampicillin,
CMV promoter is the promoter of cytomegalovirus early genes,
Kozak sequence is intended to enhance the translation efficiency of protein,
START codon is a start codon,
NLS refers to nuclear localization signals (NLS),
PaCas9 is a nucleotide sequence of SEQ ID NO: 1 encoding PaCas9 nuclease having an amino acid sequence of SEQ ID NO: 2, FLAG is a FLAG epitope sequence used for protein detection, GFP is the modified green fluorescent protein, TK pA refers to a thymidine kinase poly-A signal sequence used to increase mRNA stability F1 ori is an origin of replication which allows packaging of phagemid into phage particles when cotransformed with helper phages, polIII term+U6 promoter refers to cassettes for the expression of small RNA molecules, each cassette contains U6 promoter and RNA polymerase III transcription terminator.

pUC origin is pUC replication origin in bacteria.

FIG. 2. Amino acid sequence of PaCas9 nuclease with domain distribution of SEQ ID NO:2

DESCRIPTION OF THE INVENTION

Definitions and General Methods

Unless defined otherwise, all technical and scientific terms used herein have the same meaning as is commonly understood by one of ordinary skill in the art.

Further, unless otherwise required by context, singular terms shall include pluralities and plural terms shall include the singular. Typically, the classification and methods of cell culture, molecular biology, immunology, microbiology, genetics, analytical chemistry, organic synthesis chemistry, medical and pharmaceutical chemistry, as well as hybridization and chemistry of protein and nucleic acids described herein are well known and widely used by those skilled in the art. Enzyme reactions and purification methods are performed according to the manufacturer's instructions, as is common in the art, or as described herein.

A "mammal" refers to any animal that is classified as a mammal, including primates, humans, rodents, dogs, cats, cattle, small cattle, horses, pigs, etc.

Nuclease

Nucleases are a broad group of enzymes that hydrolyze the phosphodiester bonds between nucleic acid subunits.

Depending on their specificity and activity, nucleases can be of the following types: exonucleases and endonucleases, ribonucleases and deoxyribonucleases, restrictases and some others. Restrictases are an important element in applied molecular biology.

PaCas9 nuclease relates to the type of deoxyribonucleases.

PaCas9 nuclease is capable of cleaving DNA comprising a target nucleic acid sequence, when binding to at least one RNA molecule that recognizes the target sequence.

PaCas9 nuclease comprises two endonuclease domains, which, one by one, make single-strand breaks, and, when acting together, make a double-strand break.

PaCas9 nuclease is an effector enzyme of the type II CRISPR-Cas system (nuclease of type 2).

PaCas9 nuclease is capable of making a double-strand DNA break with a highly specific recognition site (16-20 letters).

DNA of PaCas9 nuclease is presented in SEQ ID NO:1.

Amino acid sequence of PaCas9 nuclease is presented in SEQ ID NO: 2.

FIG. 2 shows an amino acid sequence of PaCas9 nuclease with domain distribution.

PaCas9 nuclease is associated with clustered regularly interspaced short palindromic repeats (CRISPR), as well as other adjacent components of the CRISPR-Cas system: crRNA and tracrRNA sequences.

A nucleotide sequence encoding tracrRNA is presented in SEQ ID NO: 3.

A nucleotide sequence encoding a direct repeat DR is presented in SEQ ID NO: 4.

crRNA consists of a target-dependent variable part and a direct repeat DR presented in SEQ ID NO: 4.

The term "therapeutic agent" herein refers to PaCas9 nuclease having an amino acid sequence of SEQ ID NO: 2 or to an isolated nucleic acid molecule encoding the PaCas9 nuclease and having a nucleotide sequence of SEQ ID NO: 1.

tracrRNA (trans-activating crRNA) is a small trans-encoded RNA.

CRISPR (Clustered Regularly Interspaced Short Palindromic Repeats) are special bacterial and archaeal loci consisting of direct repeats that are interspaced with unique sequences (spacers).

Nucleic Acid Molecules

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, determining a fragment or a region of a nucleic acid, containing unnatural nucleotides or not, and being either a double-strand DNA or RNA, a single-stranded DNA or RNA, or transcription products of said DNAs.

It should also be included here that the present invention does not relate to nucleotide sequences in their natural chromosomal environment, i.e., in a natural state. The sequences of the present invention have been isolated and/or purified, i.e., they were sampled directly or indirectly, for example by a copy, their environment having been at least partially modified. Thus, isolated nucleic acids obtained by recombinant genetics, by means, for example, of host cells, or obtained by chemical synthesis should also be mentioned here.

An "isolated" nucleic acid molecule is one which is identified and separated from at least one nucleic acid molecule-impurity, which the former is bound to in the natural source of nuclease nucleic acid. An isolated nucleic acid molecule is different from the form or set in which it is found under natural conditions. Thus, an isolated nucleic acid molecule is different from a nucleic acid molecule that exists in cells under natural conditions. An isolated nucleic acid molecule however includes a nucleic acid molecule located in cells in which the antibody is normally expressed, for example, if the nucleic acid molecule has a chromosomal localization that is different from its localization in cells under natural conditions.

The term "nucleotide sequence" encompasses the complement thereof unless otherwise specified. Thus, a nucleic acid having a particular sequence should be understood as one which encompasses the complementary strand thereof with the complementary sequence thereof.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader sequence is operably linked to DNA for a polypeptide if it is expressed as a preprotein that participates in the secretion of the polypeptide; a promoter or enhancer is operably linked to a coding sequence if it affects the transcription of the sequence; a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

Vector

The term "vector" as used herein means a nucleic acid molecule capable of transporting another nucleic acid to which it has been linked. In some embodiments, a vector is a plasmid, i.e., a circular double-strand piece of DNA into which additional DNA segments may be ligated. In some embodiments, a vector is a viral vector, wherein additional DNA segments may be ligated into the viral genome. In some embodiments, vectors are capable of autonomous replication in a host cell into which they are introduced (e.g., bacterial vectors having a bacterial origin site of replication and episomal mammalian vectors). In further embodiments, vectors (e.g., non-episomal mammalian vectors) can be integrated into the genome of a host cell upon introduction into a host cell, and thereby are replicated along with the host gene. Moreover, certain vectors are capable of directing the expression of genes to which they are operatively linked. Such vectors are referred to herein as "recombinant expression vectors" (or simply, "expression vectors").

In one aspect, the present invention relates to a vector suitable for the expression of any of nucleotide sequences described herein.

The present invention relates to vectors comprising nucleic acid molecules that encode PaCas9 nuclease.

In some embodiments, the PaCas9 nuclease of the invention is expressed by inserting DNA into expression vectors, so that the genes are functionally linked to the necessary expression control sequences, transcriptional and translational control sequences. Expression vectors include plasmids, retroviruses, adenoviruses, adeno-associated viruses (AAV), plant viruses, such as cauliflower mosaic virus, tobacco mosaic virus, cosmids, YACs, EBV derived episomes, and the like. DNA molecules may be ligated into a vector such that transcriptional and translational control sequences within the vector serve their intended function of regulating the transcription and translation of the DNA. An expression vector and expression control sequences may be chosen to be compatible with the expression host cell used. DNA molecules can be introduced into an expression vector by standard methods (e.g., ligation of complementary restriction sites on an PaCas9 nuclease gene fragment and vector, or blunt end ligation if no restriction sites are present).

In addition to the PaCas9 nuclease gene, the recombinant vector expression of the invention can carry regulatory sequences that control the expression of the PaCas9 nuclease gene in a host cell. It will be understood by those skilled in the art that the design of an expression vector, including the selection of regulatory sequences, may depend on such factors as the choice of a host cell to be transformed, the level of expression of a desired protein, and so forth. Preferred control sequences for an expression host cell in mammals include viral elements that ensure high levels of protein expression in mammalian cells, such as promoters and/or enhancers derived from a retroviral LTR, cytomegalovirus (CMV) (such as a CMV promoter/enhancer), simian virus 40 (SV40) (such as a SV40 promoter/enhancer), adenovirus, (e.g., the major late promoter adenovirus (AdMLP)), polyomavirus and strong mammalian promoters such as native immunoglobulin promoter or actin promoter. For further description of viral control elements and sequences thereof, see, e.g., U.S. Pat. Nos. 5,168,062, 4,510, 245 and 4, 968, 615. Methods for expressing polypeptides in bacterial cells or fungal cells, e.g., yeast cells, are also well known in the art.

In addition to the PaCas9 nuclease gene and regulatory sequences, the recombinant expression vectors of the invention may carry additional sequences, such as sequences that regulate replication of a vector in host cells (e.g., origins of replication) and selectable marker genes. The selectable marker gene facilitates the selection of host cells into which a vector has been introduced (see e.g., U.S. Pat. Nos. 4,399,216, 4,634,665 and 5,179,017). For example, typically the selectable marker gene confers resistance to medicinal agents, such as G418, hygromycin or methotrexate, on a host cell into which a vector has been introduced. For example, selectable marker genes include a dihydrofolate reductase (DHFR) gene (for use in dhfr-host cells during methotrexate selection/amplification), a neo gene (for G418 selection), and a glutamate synthetase gene.

The term "expression control sequence" as used herein is intended to refer to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include the promoter of ribosome binding site, and transcription termination sequences; in eukaryotes, typically, such control sequences include promoters and transcription termination sequences. The term "control sequences" is intended to include at least all components, the presence of which is essential for expression and processing, and can also include additional components, the presence of which is advantageous, for example, leader sequences and fusion partner sequences.

Host Cells

The term "recombinant host cell" (or simply "host cell") as used herein is intended to refer to a cell into which a recombinant expression vector has been introduced. The present invention relates to host cells, which may include, for example, a vector according to the invention described above. It should be understood that "recombinant host cell" and "host cell" are intended to refer not only to a particular subject cell but to the progeny of such a cell as well. Since modifications may occur in succeeding generations due to either mutation or environmental influences, such progeny may not, in fact, be identical to a parental cell, however, such cells are still included within the scope of the term "host cell" as used herein.

Nucleic acid molecules encoding PaCas9 nuclease of the invention and vectors comprising these nucleic acid molecules can be used for transfection of a suitable mammalian or cell thereof, plant or cell thereof, bacterial or yeast host cell. Transformation can be by any known technique for introducing polynucleotides into a host-cell. Methods for introduction of heterologous polynucleotides into mammalian cells are well known in the art and include dextran-mediated transfection, cationic polymer-nucleic acid complex transfection, calcium phosphate precipitation, polybrene-mediated transfection, protoplast fusion, encapsulation of the polynucleotide(s) in liposomes, and direct microinjection of DNA into nuclei. In addition, nucleic acid molecules may be introduced into mammalian cells by viral vectors. Methods for transfecting cells are well known in the art. See, e.g., U. S. Pat. Nos. 4,399,216, 4,912,040, 4,740,461 and 4,959,455. Methods for transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines used as hosts for transformation are well known in the art and include a plurality of immortalized cell lines available. These include, e.g., Chinese hamster ovary (CHO) cells, NS0 cells, SP2 cells, HEK-293T cells, FreeStyle 293 cells (Invitrogen), NIH-3T3 cells, Hela cells, baby hamster kidney (BHK) cells, African monkey green kidney cells (COS), human hepatocellular carcinoma cells (e.g., Hep G2), A549 cells, and a number of other cell lines. Cell lines are selected by determining which cell lines have high expression levels and provide for necessary characteristics of protein produced. Other cell lines that may be used are insect cell lines, such as Sf9 or Sf21 cells. When recombinant expression vectors encoding the PaCas9 nuclease are introduced into mammalian host cells, the PaCas9 nuclease are produced by culturing the host cells for a period of time sufficient to allow for expression of the PaCas9 nuclease in host cells or, more preferably, secretion of the PaCas9 nuclease into the culture medium in which the host cells are grown. The PaCas9 nuclease can be isolated from the culture medium using standard protein purification techniques. Plant host cells include, e.g., *Nicotiana*, *Arabidopsis*, duckweed, corn, wheat, potato, etc. Bacterial host cells include *Escherichia* and *Streptomyces* species. Yeast host cells include *Schizosaccharomyces pombe*, *Saccharomyces cerevisiae* and *Pichia pastoris*.

Furthermore, level of production of the PaCas9 nuclease of the invention from production cell lines can be enhanced using a number of known techniques. For example, the glutamine synthetase gene expression system (the GS system) is a common approach for enhancing expression under certain conditions. The GS system is discussed in whole or part in connection with EP Nos. 0216846, 0256055, 0323997 and 0338841.

It is likely that the PaCas9 nuclease obtained from different cell lines or from transgenic animals will have a different glycosylation profile as compared to each other. However, the PaCas9 nuclease encoded by the nucleic acid molecules described herein is part of the present invention, regardless of the glycosylation state, and, in general, regardless of the presence or absence of post-translational modifications.

Liposome

In one aspect, the present invention relates to liposomes encapsulating the PaCas9 nuclease having an amino acid sequence of SEQ ID NO: 2 or to an isolated nucleic acid molecule encoding the PaCas9 nuclease and having a nucleotide sequence of SEQ ID NO: 1.

Liposomes are microscopic closed vesicles having an internal phase, surrounded by one or more lipid bilayers, and ability to hold water-soluble material in the internal phase, and oil-soluble material in the phospholipid bilayer. When entrapping an active compound in liposome, and delivering it to target tissue, how to entrap the active compound in the liposome with high efficiency, and how to secure stable retention of the active compound by the liposome constitute important issues.

In general, a liposome is considered a particle with a predominant size of several tens of nanometers up to tenths of a micron, its shell accommodating molecules of another substance(s). The liposome shell is "semi-permeable" to water molecules and ions.

Liposomes are characterized by the ability to contain and retain substances of different nature. The range of substances incorporated in liposomes is quite wide, ranging from inorganic ions and low-molecular-weight organic compounds to large proteins and nucleic acids.

Liposomes provide a prolonged release of a substance incorporated in a carrier.

Liposomes can be made from phospholipid, in particular from phosphatidylcholine, phosphatidylethanolamine, phosphatidylserine, phosphatidylinositol, phosphatidylglycerol, phosphatidic acid, sphingophospholipid, egg/soybean phospholipids or mixtures thereof.

EXAMPLES

The following examples are provided for better understanding of the invention. These examples are for purposes of illustration only and are not to be construed as limiting the scope of the invention in any manner.

All publications, patents, and patent applications cited in this specification are incorporated herein by reference. Although the foregoing invention has been described in some detail by way example: for of illustration and purposes of clarity of understanding, it will be readily apparent to those of ordinary skill in the art in light of the teachings of this invention that certain changes and modifications may be made thereto without departing from the spirit or scope of the appended embodiments.

Materials and General Methods

Recombinant DNA Techniques

Standard methods were used to manipulate DNA as described in Sambrook, J. et al, Molecular cloning: A laboratory manual; Cold Spring Harbor Laboratory Press, Cold Spring Harbor, New York, 1989. The molecular biological reagents were used according to the manufacturer's instructions.

Gene Synthesis

Desired gene segments were prepared from oligonucleotides made by chemical synthesis. The gene segments of 300-4000 kb long, which were flanked by singular restriction sites, were assembled by annealing and ligation of oligonucleotides including PCR amplification and subsequently cloned via the indicated restriction sites. The DNA sequences of the subcloned gene fragments were confirmed by DNA sequencing.

DNA Sequence Determination DNA sequences were determined by Sanger sequencing.

DNA and Protein Sequence Analysis and Sequence Data Management

The Infomax's Vector NTI Advance suite version 8.0 was used for sequence creation, mapping, analysis, annotation and illustration.

Expression Vectors

For the expression of the PaCas9 nuclease, variants of expression plasmids intended for expression in prokaryotic cells (*E. coli*), transient expression in eukaryotic cells (e.g., in CHO cells) were used. Beside the PaCas9 nuclease expression cassette the vectors contained: an origin of replication which allows replication of said plasmid in *E.* coli, genes which confer resistance in E. coli to various antibiotics (e.g., to ampicillin and/or kanamycin).

Example 1

Method of Preparation of PaCas9 Nuclease

To prepare metagenomic sequences, samples of Homoeodictya palmata sponges were collected from regions of the White Sea, the material was fractionated by centrifugation, then total DNA was isolated and subsequently sequenced.

An open reading frame of the PaCas9 protein, as well as adjacent components of CRISPR-Cas system (CRISPR cassette, as well as crRNA and tracrRNA sequences) were detected in the metagenomic sequences using bioinformatics methods.

DNA of PaCas9 nuclease is presented in SEQ ID NO:1.

The amino acid sequence of PaCas9 nuclease is presented in SEQ ID NO:2.

A nucleotide sequence encoding tracrRNA is presented in SEQ ID NO: 3.

A nucleotide sequence encoding a direct repeat DR is presented in SEQ ID NO: 4.

Example 2

Description of Cloning

The PaCas9 nuclease gene sequence was obtained by way of bioinformatic search. The sequence was codon-optimized to ensure optimal expression in mammalian cells, and then assembled de novo from chemically synthesized oligonucleotides using the Gibson method. The synthesized PaCas9 gene was cloned in a genetic construct from the 3'-end of the CMV promoter. Kozak sequences and nuclear localization signals (NLS) were added from the 5'-end of the gene, and FLAG epitope sequence for protein detection was added from the 3'-end. After the PaCas9 sequence and its associated elements as listed above, T2A elements and the open reading frame of the green fluorescent protein (EGFP) as a marker for expression are placed in the construct in the same reading frame.

After the reading frames, a thymidine kinase poly-A signal sequence is placed from the 3'-end to increase the stability of mRNA. There are two cassettes in tandem in the area of the bacterial cortex of the genetic construct for expression of small RNA molecules. Each cassette contains a U6 promoter and RNA polymerase III transcription terminator. These cassettes are necessary for the expression of RNA molecules that provide specific interaction of the PaCas9 protein with the target DNA molecule (cellular genome). The construct map is shown in FIG. 1. This construct allows for expressing both the PaCas9 protein (which is transported to the nucleus through NLS) and RNA molecules guiding the protein (guiding RNAs), as well as detecting the protein by FLAG epitope and determining the efficiency of delivery of the genetic construct by detection of EGFP.

Example 3

Enzymatic Activity of PaCas9 Protein

Amino acids involved in enzymatic hydrolysis of DNA/RNA were identified by comparing the homology of HNH and RuvC domains of various Cas9 family proteins with PaCas9 domains (domain distribution is shown in FIG. 2). Conservative amino acids, for which participation in the enzymatic activity of Cas9 proteins was previously shown, were isolated in PaCas9. Thus, it was found by analytical methods that the amino acid residues of this protein are necessary for the enzymatic activity of PaCas9 protein (amino acid-position): D 9; E 527; H 750; D 753; H 613; N 636.

Example 4

Determination of Enzymatic Activity of PaCas9 Protein

To determine PAM (Protospacer Adjacent Motif) sequence, we performed in vitro reactions of cutting DNA libraries using a recombinant nuclease protein (SEQ ID NO: 2), crRNA (consists of a target-dependent variable part and a direct repeat presented in SEQ ID NO: 4) and tracrRNA (SEQ ID NO:3). DNA library is a PCR fragment comprising a seven-letter randomized sequence, and a recognizable sequence, a protospacer.

After incubation of PaCas9-RNA-protein complex with the DNA library, the products reaction are into loaded gel electrophoresis. Uncut fragments are extracted from the gel and sequenced on Illumina platform. Comparison of PAM sequences contained in uncut PaCas9 reaction products and a control reaction will allow to determine PAM of protein in question.

After identifying the PAM sequence, in vitro nuclease activity is evaluated. To this end, protein in complex with RNA guides is incubated with a DNA fragment carrying a protospacer sequence and identified PAM. Optimal ratio of the RNA-protein complex to cut DNA was determined. Nuclease activity was evaluated based on the amount of PaCas9 protein, required for 50% cutting of 200 ng of target DNA of about 400 base pairs long, containing the optimal PAM.

Thus, it was confirmed that PaCas9 nuclease has enzymatic activity and makes a double-strand break in DNA.

Moreover, it was confirmed that PaCas9 nuclease is able to make a double-strand break in DNA with a highly specific recognition site (16-20 letters).

The invention claimed is:

1. An expression vector comprising:
   a beta-lactamase gene;
   a promoter of cytomegalovirus early genes;
   a Kozak sequence;
   a start codon;
   nuclear localization signals (NLS);
   the nucleotide sequence of SEQ ID NO: 1;
   a FLAG epitope sequence;
   a modified green fluorescent protein;
   a thymidine kinase poly-A signal sequence;
   an origin of replication, cassettes for the expression of small RNA molecules, each cassette containing a U6 promoter and an RNA polymerase Ill transcription terminator; and
   pUC replication origin in bacteria.

2. A liposome for delivering an agent comprising a nuclease comprising the amino acid sequence of SEQ ID NO: 2 or the nucleic acid sequence of SEQ ID NO: 1.

3. A method for delivery of an agent to a target cell or target tissue comprising introducing the liposome of claim 2 into a target cell or a target tissue in vitro.

4. A method for producing an isolated host cell for producing a nuclease including the amino acid sequence of SEQ ID NO: 2, comprising transforming a cell with the liposome of claim 2.

5. A method of delivering an agent to a target cell or target tissue comprising introducing a vector comprising an isolated nucleic acid comprising the nucleotide sequence of SEQ ID NO: 1 into the target cell or target tissue.

6. A method for producing an isolated host cell for producing a nuclease including the amino acid sequence of SEQ ID NO: 2, comprising transforming the cell with a vector comprising an isolated nucleic acid comprising the nucleotide sequence of SEQ ID NO: 1.

7. An isolated host cell for producing a nuclease that includes the amino acid sequence of SEQ ID NO: 2, the isolated host cell comprising a heterologous nucleic acid comprising the nucleotide sequence of SEQ ID NO: 1.

8. A method for producing a nuclease including the amino acid sequence of SEQ ID NO: 2, comprising culturing the host cell of claim 7 in a growth medium under conditions sufficient to produce said nuclease, followed by isolation and purification of the obtained nuclease.

* * * * *